United States Patent [19]

Sklavounos et al.

[11] Patent Number: 5,665,708

[45] Date of Patent: Sep. 9, 1997

[54] PROCESS AND ANTIPARASITIC INTERMEDIATES FOR DORAMECTIN

[75] Inventors: Constantine Sklavounos, Waterford; Thomas Charles Crawford, Ledyard; Neil Demers, Clinton, all of Conn.; Stephen Paul Gibson, Westbrook, England; Charles William Murtiashaw, deceased, late of North Stonington, Conn., by Martha Murtiashaw, Administratrix

[73] Assignee: Pfizer Inc., New York, N.Y.

[21] Appl. No.: 617,740

[22] PCT Filed: Sep. 19, 1994

[86] PCT No.: PCT/IB94/00283

§ 371 Date: Mar. 8, 1996

§ 102(e) Date: Mar. 8, 1996

[87] PCT Pub. No.: WO95/09863

PCT Pub. Date: Apr. 13, 1995

Related U.S. Application Data

[63] Continuation of Ser. No. 131,812, Oct. 5, 1993, abandoned.

[51] Int. Cl.$^6$ .............. A61K 31/70; C07H 17/08
[52] U.S. Cl. ................................. 514/30; 536/7.1
[58] Field of Search ..................... 514/30; 536/7.1

[56] References Cited

U.S. PATENT DOCUMENTS

| | | | |
|---|---|---|---|
| 4,201,861 | 5/1980 | Mrozik et al. | 536/17 A |
| 4,328,335 | 5/1982 | Mrozik | 536/7.1 |
| 4,457,920 | 7/1984 | Mrozik et al. | 424/180 |
| 4,806,527 | 2/1989 | Christensen et al. | 514/30 |
| 4,886,828 | 12/1989 | Asato et al. | 514/450 |
| 4,980,370 | 12/1990 | Dutton et al. | 514/450 |
| 4,992,424 | 2/1991 | Banks et al. | 514/30 |
| 5,023,241 | 6/1991 | Linn et al. | 514/30 |
| 5,057,498 | 10/1991 | Dutton et al. | 514/30 |
| 5,089,480 | 2/1992 | Gibson et al. | 514/30 |
| 5,112,746 | 5/1992 | Dutton et al. | 435/100 |
| 5,162,363 | 11/1992 | Meinke et al. | 514/433 |
| 5,208,222 | 5/1993 | Meinke et al. | 514/30 |
| 5,229,415 | 7/1993 | Linn et al. | 514/450 |
| 5,229,416 | 7/1993 | Meinke et al. | 514/450 |
| 5,262,400 | 11/1993 | Chu et al. | 514/30 |
| 5,556,868 | 9/1996 | Banks | 514/450 |
| 5,578,581 | 11/1996 | Masurekar et al. | 514/30 |

FOREIGN PATENT DOCUMENTS

| | | |
|---|---|---|
| 0215654 | 3/1987 | European Pat. Off. |
| 0259688 | 3/1988 | European Pat. Off. |
| 0276103 | 7/1988 | European Pat. Off. |

OTHER PUBLICATIONS

Mrozik, et al., "Partial Synthesis of Avermectin $B_{1a}$ from Avermectin $B_{2a}$", Tetrahedron Letters, 1982, 23, 2377–78.

Dutton et al., "Novel Avermectins Produced by Mutational Biosynthesis," Journal of Antibiotics, 1991, 44, 357–65.

Hafner et al., "Branched–chain Fatty Acid Requirement for Avermectin Production by a Mutant of *Streptomyces Avermitilis* Lacking Branched–chain 2–oxo Acid Dehydrogenase Activity", Journal of Antibiotics 1991, 44, 349–56.

Gration et al., Veterinary Parasitology, 42, 1992, pp. 273–279.

*Primary Examiner*—John Kight
*Assistant Examiner*—Howard C. Lee
*Attorney, Agent, or Firm*—Peter C. Richardson; Gregg C. Benson; Robert T. Ronau

[57] ABSTRACT

Intermediates and a process for preparing doramectin, the compound of formula (I), semisynthetically from by-product in the fermentation procedure which also yields the compound of formula (I). The intermediates prepared by the process of this invention also have utility as antiparasitic agents. The process of this invention utilizes continuous reaction inert gas sparging during the pyrolysis step, resulting in a significant improvement in the overall yield of this conversion.

23 Claims, No Drawings

PROCESS AND ANTIPARASITIC INTERMEDIATES FOR DORAMECTIN

This is the national stage under 35 U.S.C. §371 (c) and 37 C.F.R. 1.491 of International Application No. PCT/IB94/00283, filed Sep. 19, 1994, which was originally filed Oct. 5, 1993 as U.S. Ser. No. 08/131,812 (now abandoned).

BACKGROUND OF THE INVENTION

This invention relates to novel intermediates in the preparation of the compound of formula (I) below,

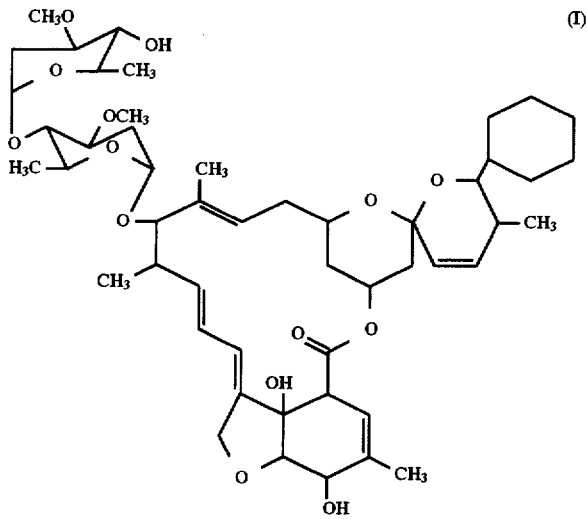

hereinafter referred to as doramectin, and improved processes for preparing said intermediates. The invention also relates to the utility of said intermediates as antiparasitic compounds in their own right. The invention further relates to an improved process for preparing doramectin from the compound of formula (II) below.

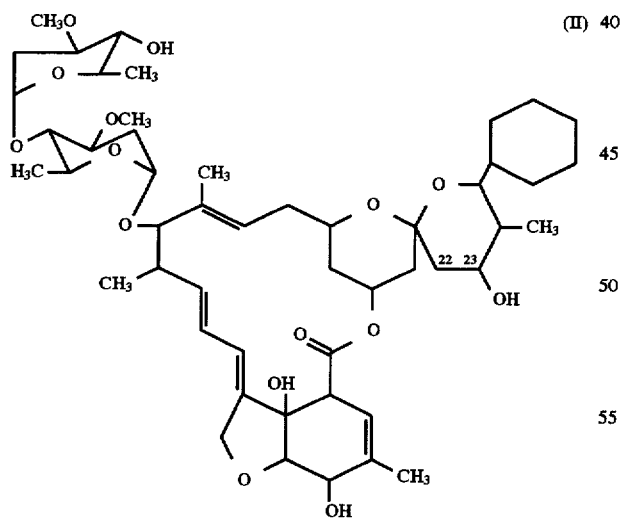

Doramectin is a broad spectrum antiparasitic and anthelmintic agent belonging to a class of secondary metabolites known as avermectins. Doramectin can be prepared by fermenting an avermectin producing strain of the microorganism *Streptomyces avermitilis* such as ATCC 31267, 31271 or 31272 under aerobic conditions in an aqueous nutrient medium containing inorganic salts and assimilable sources of carbon and nitrogen as described in U.S. Pat. No. 5,089,480, which is incorporated herein by reference. Another strain of avermectin producing microorganism is *Streptomyces avermitilis* ATCC 53568, which is described in Dutton et al., Journal of Antibiotics, 44, 357–65 (1991). *Streptomyces avermitilis* ATCC 31267, 31271, 31272 and 53568 are currently on deposit with the American Type Culture Collection, 12301 Parklawn Drive, Rockville, Md. 20852, U.S.A., under the terms of the Budapest Treaty.

During the fermentation procedure which produces the compound of formula (I) hereinabove various co-products can be isolated. A major co-product which can be isolated during the fermentation of the above-identified microorganisms has the structure of formula (II) hereinabove. The isolation of the compound of formula (II) from the fermentation broth of *Streptomyces avermitilis* ATCC 53568 is described in Dutton et al., Id. The compound of formula (II) is an active antiparasitic and anthelmintic compound which has been disclosed and claimed in U.S. Pat. No. 5,089,480. However, doramectin is preferred. The process of the present invention makes use of the co-product of formula (II) by converting it into the more valuable antiparasitic agent doramectin of formula (I).

The overall transformation in this process is the elimination of the C-23 hydroxyl group, leaving an olefin in the C-22 to C-23 positions of the molecule. Low yield processes which effect the same transformation on slightly different avermectins have been reported. For example, where the C-25 cyclohexyl group is instead a sec-butyl group, the transformation has been achieved using a five step sequence in approximately 3.6% overall yield. Mrozik et al., *Tetrahedron Letters*, 1982, 23, 2377–78. In light of the low yield of this prior art process, it is desirable to devise a process whereby the starting material is more efficiently converted to doramectin.

Therefore, it is an object of this invention to convert the compound of formula (II) to doramectin in high overall yield. It is a further object of this invention to provide useful intermediates for the process.

SUMMARY OF THE INVENTION

The present invention provides novel intermediates of the formula (III)

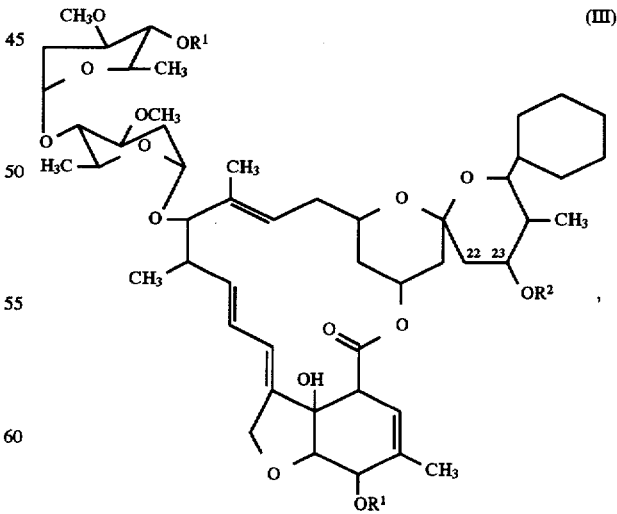

wherein $R^1$ is $(C_2-C_5)$alkanoyl, or aryloxyacetyl and $R^2$ is hydrogen or aryloxythiocarbonyl.

This invention further provides novel intermediates of the formula (IV):

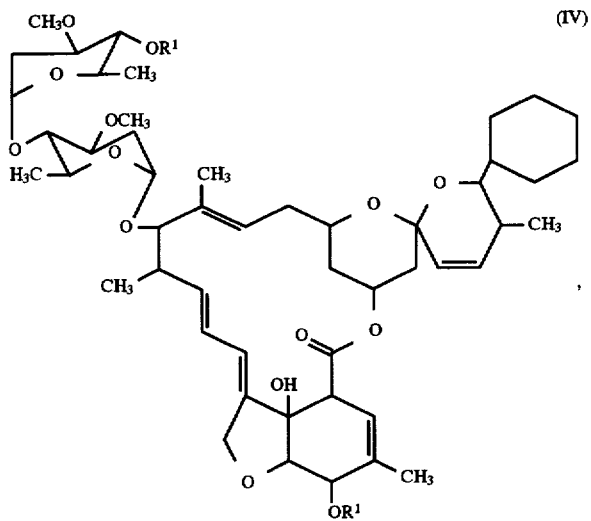

(IV)

wherein $R^1$ is $(C_2-C_5)$alkanoyl or aryloxyacetyl.

Particularly preferred compounds of this invention are those compounds of formula (III) wherein $R^1$ is $(C_2-C_5)$ alkanoyl, phenoxyacetyl or $(C_1-C_4)$alkylphenoxyacetyl and $R^2$ is hydrogen or $(C_1-C_4)$alkylphenoxythiocarbonyl. Especially preferred compounds within this group are the compounds of formula (III) wherein $R^1$ is acetyl or phenoxyacetyl and $R^2$ is hydrogen or p-tolyloxythiocarbonyl.

Also particularly preferred compounds of this invention are the compounds of formula (IV) wherein $R^1$ is $(C_2-C_5)$ alkanoyl, phenoxyacetyl or $(C_1-C_4)$alkylphenoxyacetyl. Especially preferred compounds within this group are the compounds of formula (IV) wherein $R^1$ is acetyl or phenoxyacetyl.

This invention further provides a process for preparing a compound of formula (I).

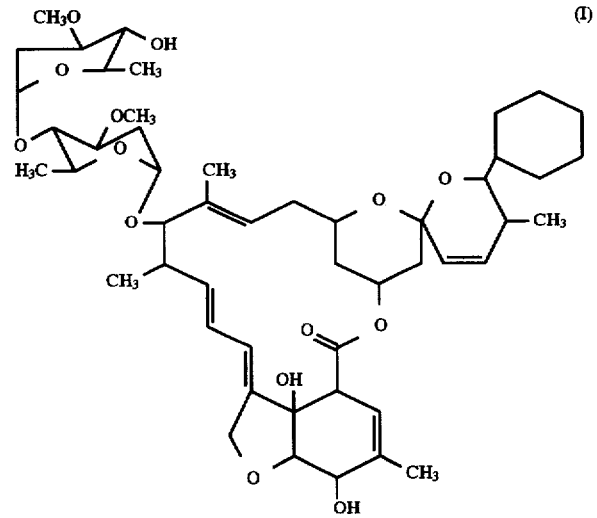

(I)

comprising the consecutive steps of (a) reacting a compound of formula (II),

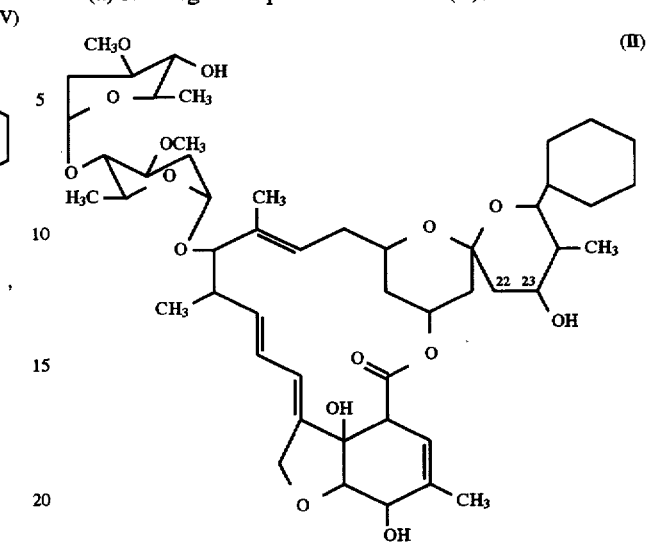

(II)

with an acylating agent of the formula $(R^4CO)_2O$ or $R^4COX$ wherein $R^4$ is aryloxymethyl and X is Cl or Br to form the compound according to formula (III) wherein $R^1$ is aryloxyacetyl and $R^2$ is H;

(b) reacting said compound of formula (III) wherein $R^1$ is aryloxyacetyl and $R^2$ is H with a compound of the formula $R^3OC(=S)X$, wherein $R^3$ is aryl and X is Cl or Br to form the compound according to formula (III) wherein $R^1$ is aryloxyacetyl and $R^2$ is aryloxythiocarbonyl;

(c) reacting said compound of formula (III) wherein $R^1$ is aryloxyacetyl and $R^2$ is aryloxythiocarbonyl in a reaction inert solvent at from about 150° C. to about 200° C. for about 2 hours to about 48 hours in the presence of calcium carbonate under continuous reaction inert gas sparging to form the compound according to formula (IV) wherein $R^1$ is aryloxyacetyl; and (d) reacting said compound of formula (IV) wherein $R^1$ is aryloxyacetyl with a base in an alcohol solvent to form the compound according to formula (I).

A particularly preferred process within this process is the process wherein said reaction inert gas is nitrogen. An especially preferred process within this particularly preferred process is the process wherein the base is $NH_3$, KOH, KCN, $Na_2CO_3$, $NaHCO_3$, or NaOAc. Even more particularly preferred processes within the especially preferred process are those processes which utilize the particularly preferred compounds of this invention.

This invention is further directed to a process for preparing a compound of formula (I) comprising the consecutive steps of (a) reacting a compound of formula (II) with an acylating agent of the formula $(R^4CO)_2O$ or $R^4COX$ wherein $R^4$ is $(C_1-C_4)$alkyl, and X is Cl or Br to form the compound according to formula (III) wherein $R^1$ is $(C_1-C_4)$ alkanoyl and $R^2$ is H;

(b) reacting said compound of formula (III) wherein $R^1$ is $(C_1-C_4)$alkanoyl and $R^2$ is H with a compound of the formula $R^3OC(=S)X$ wherein $R^3$ is aryl and X is Cl or Br to form the compound according to formula (III) wherein $R^1$ is $(C_1-C_4)$alkanoyl and $R^2$ is aryloxythiocarbonyl;

(c) reacting said compound of formula (III) wherein $R^1$ is $(C_1-C_4)$alkanoyl and $R^2$ is aryloxythiocarbonyl in a reaction inert solvent at from about 150° C. to about 200° C. for about 2 hours to about 48 hours in the presence of calcium carbonate under continuous reaction inert gas sparging to form the compound according to formula (IV) wherein $R^1$ is $(C_1-C_4)$alkanoyl; and (d) reacting said compound of formula (IV) wherein $R^1$ is $(C_1-C_4)$alkanoyl with lithium aluminum hydride, sodium cyanoborohydride or lithium triethylborohydride in a reaction inert solvent to form the compound according to formula (I).

A particularly preferred process within this process is that process wherein the reaction inert gas is nitrogen. Even more particularly preferred processes within this particularly preferred process are those processes which utilize the particularly preferred compounds of this invention.

This invention further provides a method of treating mammals suffering from a parasitic disease comprising administering to said mammal an antiparasitic effective amount of a compound of formula (III) or (IV).

DETAILED DESCRIPTION OF THE INVENTION

The compounds of the present invention are readily prepared according to the process of the present invention which is described in detail hereinbelow.

The compound of formula (I) of this invention is doramectin, a useful antiparasitic and anthelmintic agent which is described in U.S. Pat. No. 5,089,480, incorporated herein by reference. Doramectin is prepared from the compound of formula (IV) hereinabove of the present invention by reacting said compound of formula (IV) with lithium aluminumhydride, sodium cyanoborohydride or lithium triethylborohydride or by saponifying the ester, depending upon the nature of the ester to be cleaved.

In the case where $R^1$ is $(C_2-C_5)$alkanoyl, the $(C_2-C_5)$ alkanoyloxy group is converted to a hydroxy group by reacting said compound of formula (IV) wherein $R^1$ is $(C_2-C_5)$alkanoyl with lithium aluminum hydride, sodium cyanoborohydride or lithium triethylborohydride in a reaction inert solvent at a temperature of about $-100°$ C. to about $0°$ C. for about 15 minutes to about 24 hours. Suitable reaction inert solvents for this reaction will depend upon the choice of reducing agent and will be selected from but not limited to such solvents as diethyl ether, dioxane, tetrahydrofuran, 2-methoxymethyl ether and 1,2-dimethoxyethane. A particularly preferred reducing agent for this reaction is lithium triethylborohydride and a particularly good solvent is tetrahydrofuran. Generally a temperature of $-78°$ C. to $-70°$ C. is maintained during the course of the mixing of the reagent with the substrate and for a short time, usually about 15 minutes to one hour, thereafter. Shortly after the mixing is complete, usually within 15 minutes to one hour, the temperature is allowed to rise slowly to ambient temperature. The reaction mixture is quenched and the product compound of formula (I) is isolated according to standard procedures known to one of ordinary skill in the art.

In the case where $R^1$ is aryloxyacetyl the aryloxyacetyloxy group is converted to a hydroxy group by reacting said compound of formula (IV) wherein $R^1$ is aryloxyacetyl with an alkali metal hydroxide in an alcoholic solvent at a temperature of about $-75°$ C. to about $0°$ C. for about 15 minutes to about 24 hours. A particularly preferred alkali metal hydroxide is potassium hydroxide and a particularly preferred solvent is methanol. Generally the reaction is performed at a temperature of $-35°$ C. for about one hour, after which time the compound of formula (I) is isolated according to standard procedures known to one of ordinary skill in the art. Alternatively this reaction can be performed by substituting ammonia for the alkali metal hydroxide. In the cases where ammonia is used the reaction is generally performed at about $-35°$ C. to about $0°$ C. for about one hour to about 16 hours. The reaction is preferably run in methanol at $-15°$ C. for about five to six hours. The product compound of formula (I) is isolated according to standard procedures of organic chemistry well known to one of ordinary skill in the art.

The compounds of formula (IV) of the present invention are readily prepared according to the process of this invention by reacting a compound of formula (III) of this invention in a high-boiling solvent such as but not limited to 2-methoxyethyl ether or 2-ethoxyethyl ether at a temperature of about 150° C. to about 200° C. for about 2 hours to about 48 hours. To obtain maximum yield the reaction mixture is continuously sparged with a reaction inert gas such as nitrogen or argon. It is particularly preferred to perform the reaction at 156° C.–158° C. in 2-methoxyethyl ether with continuous nitrogen gas sparging for 12 hours. When the reaction is complete the product compound of formula (IV) is isolated according to the standard methods known to one of ordinary skill in the art.

The compounds of formula (III) of the present invention wherein $R^2$ is aryloxythiocarbonyl are prepared according to the process of this invention by reacting a compound of formula (III) of the present invention wherein $R^2$ is hydrogen with a halothionoformate of the formula $R^3OC(=S)X$, wherein $R^3$ is as defined above, in a reaction inert solvent in the presence of a proton scavenger such as pyridine or 4-dimethylaminopyridine for about 30 minutes to about 12 hours. Suitable reaction inert solvents for this reaction include ethyl acetate, 1,2-dimethoxyethane, 2-methoxymethyl ether, 2-methoxyethyl ether, aromatic solvents such as toluene, xylene and benzene and chlorinated solvents such as chloroform and methylene chloride. Preferred solvents for this reaction are ethyl acetate or toluene. It is preferred to allow the reaction to operate for 2 to 4 hours. The reaction mixture is heated at from 40° C. to about the refluxing temperature of the solvent chosen for the particular reaction. The reaction mixture is quenched and the product compound of formula (III) wherein $R^2$ is aryloxythiocarbonyl is isolated according to standard methods.

The compounds of formula (III) of the present invention wherein $R^2$ is hydrogen and $R^1$ is $(C_2-C_5)$alkanoyl or aryloxyacetyl are readily prepared according to the process of this invention. The compound of formula (II) is reacted with an acylating agent in a reaction inert solvent in the presence of a proton scavenger such as but not limited to pyridine, 4-dimethylaminopyridine, piperidine, pyrrolidine, triethylamine, morpholine or diisopropylethylamine at a temperature of about $-75°$ C. to about $0°$ C. for about 5 minutes to about 8 hours. Suitable reaction inert solvents for this reaction include aromatic solvents such as toluene, benzene or xylene or chlorinated solvents such as methylene chloride, chloroform or 1,2-dichloroethane. Suitable acylating agents are either acid halides, usually acid chlorides or acid anhydrides. When an acid chloride is used as an acylating agent in this reaction, a particularly preferred organic amine is pyridine. When an acid anhydride is used as an acylating agent in this reaction, a particularly preferred organic amine is triethylamine. Generally preferred solvents for these reactions, whether using an acid chloride or an acid anhydride as the acylating agent, are chlorinated solvents. Methylene chloride is preferred particularly. When the reaction is complete, the reaction mixture is quenched and the product compound of formula (III) wherein $R^2$ is hydrogen and $R^1$ is ($C_2$-$C_5$)alkanoyl or aryloxyacetyl is isolated according to standard procedures of organic chemistry.

The compound of formula (II) can be isolated via fermentation of an avermectin producing strain of *Streptomyces avermitilis* such as ATCC 31267, 31271 or 31272, as described in U.S. Pat. No. 5,089,480, which is incorporated herein by reference. Other methods for obtaining the compound of formula (II) include isolation from the fermentation broth of *Streptomyces avermitilis* ATCC 53568, as described in Dutton et al., Journal of Antibiotics, 44, 357–65 (1991).

The novel compounds (III)–(IV) of the present invention are useful as intermediates in the synthesis of the compound of formula (I), doramectin, from the compound of formula (II).

The novel compounds (III)–(IV) of the present invention are also useful as antiparasitic agents. The utility of said compounds (III)–(IV) as antiparasitic agents is demonstrated by the activity of said compounds in an in vivo rodent model as described by Gration et al., Veterinary Parasitology, 42, 1992, 273–279.

The compounds of formulas (III) and (IV) are a highly active antiparasitic agent having particular utility as anthelmintics, ectoparasiticides, insecticides and acaricides.

The compounds of formulas (III) and (IV) are effective in treating and preventing a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. Doramectin is also effective against other nematodes which affect various species of animals including, for example, Dirofilaria in dogs and various parasites such as Ancylostoma, Necator, Ascaris, Strongyloides, Trichinella, Capillaria, Trichuris, Enterobius and parasites which are found in the blood or other tissues and organs such as filarial worms and the extra intestinal stages of Strongyloides and Trichinella.

The compounds of formulas (III) and (IV) are also of value in treating and preventing ectoparasite infections including in particular arthropod ectoparasites of animals and birds such as ticks, mites, lice, fleas, blowfly, biting insects and migrating dipterous larvae which can affect cattle and horses.

The compounds of formulas (III) and (IV) are also an insecticide active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (III) and (IV) are administered as a formulation appropriate to the specific use envisaged and to the particular species of host animal being treated and the parasite or insect involved. For use as an anthelmintic the compound may be administered orally in the form of a capsule, bolus, tablet or preferably a liquid drench, or alternatively, it may be administered by injection, pour-on or as an implant. Such formulations are prepared in a conventional manner in accordance with standard veterinary practice. Thus, capsules, boluses or tablets may be prepared by mixing the active ingredient with a suitable finely divided diluent or carrier additionally containing a disintegrating agent and/or binder such as starch, lactose, talc, magnesium stearate, etc. A drench formulation may be prepared by dispersing the active ingredient in an aqueous solution together with dispersing or wetting agents etc. and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral or injectable administration a dose of from about 0.001 to 10 mg per kg of animal body weight given as a single dose or in divided doses for a period of from 1 to 5 days will be satisfactory but of course there can be instances where higher or lower dosage ranges are indicated and such are within the scope of this invention. For oral or injectable administration a more preferred dose is about 0.02 mg to 2 mg per kg of animal body weight given as a single dose or in divided doses for a period of 1 to 5 days.

As an alternative the compounds may be administered with the animal feedstuff and for this purpose a concentrated feed additive or premix may be prepared for mixing with the normal animal feed.

For use as an insecticide and for treating agricultural pests the compounds are applied in the form of sprays, dusts, emulsions and the like in accordance with standard agricultural practice.

As used hereinabove and in the appendant claims, the term "reaction inert solvent" refers to any solvent which does not interact with starting materials, reagents, intermediates or products in a manner which adversely affects the yield of the desired product. The term "reaction inert gas" refers to any gas which does not interact with starting materials, reagents, intermediates or products in a manner which adversely affects the yield of the desired product.

As used hereinabove and in the appendant claims, the term "aryl" means phenyl or phenyl optionally substituted with one to three ($C_1$-$C_4$)alkyl, ($C_1$-$C_4$)alkoxy or halo.

As used hereinabove and in the appendant claims, the term "aryloxy" means phenoxy or phenoxy optionally substituted with one to three ($C_1$-$C_4$)alkyl, ($C_1$-$C_4$)alkoxy or halo.

The present invention is illustrated by the following examples. However, it should be understood that the invention is not limited to the specific details of these examples.

EXAMPLE 1

The compound of formula (III) wherein $R^1$ is phenoxyacetyl and $R^2$ is hydrogen A solution of 20 g of the compound of formula (II) in 400 ml methylene chloride and 10 ml anhydrous pyridine under nitrogen was cooled to −78° C. and 15.1 ml phenoxyacetyl chloride was added, dropwise, over 10 minutes. The reaction mixture was maintained at −70° to −78° C. for 1.5 hours and then quenched with 250 ml of a saturated solution of sodium bicarbonate. The mixture was stirred for 1.5 hours, the organic layer separated, re-extracted with 250 ml saturated solution sodium bicarbonate, and dried over anhydrous MgSO₄. The solvent was then removed in vacuo to give 25.7 g of 97% pure title product as an off white solid (96% yield). HPLC retention time was 7.9 minutes (Ultrasphere ODS 5μ, 25 cm×4.6 mm (Beckman); methanol:acetonitrile:water 559:383:58; 1.5 ml/min; UV 245 nm).

EXAMPLE 2

The compound of formula (III) wherein $R^1$ is phenoxyacetyl and $R^2$ is p-tolyloxythiocarbonyl A solution of 10 g of the title compound of Example 1 in 100 ml toluene and 30 ml anhydrous pyridine under nitrogen was heated to 100° C. and 7.7 ml O-p-tolylchlorothionoformate was added over 5 minutes. The mixture was maintained at 100°±5° C. for 2 hours to complete the reaction, cooled to about 50° C., and the solvents removed in vacuo to give a brown residue. This was dissolved in 120 ml toluene, the solution extracted with 120 ml water and twice with 100 ml of a saturated solution of sodium bicarbonate. The separated organic layer was condensed to about 80 ml, filtered, and chromatographed using a Prep-500 system (Waters Associates) equipped with two silica gel cartridges. The eluting solvent was 75:25 hexanes-:ethyl acetate. Fractions containing product were combined and the solvent removed in vacuo to give 9.8 g of 95.7% pure product as a light yellow-brown solid (83.2% yield). HPLC retention time was 15.2 minutes (Ultrasphere ODS 5μ, 25 cm×4.6 mm (Beckman); methanol:acetonitrile:water 559:383:58; 1.5 ml/min; UV 245 nm).

EXAMPLE 3

5,4"-O-Diphenoxyacetyl-doramectin (compound of formula IV wherein $R^1$ is phenoxyacetyl)

To a solution of 8.5 g of the title compound of Example 2 in 90 ml 2-methoxyethyl ether was added 4.5 g calcium carbonate. The mixture was then heated to 156°–158° C. with good agitation while continuously sparging with a nitrogen stream. After 24 hours at 156°–158° C., analysis of the mixture showed the presence of 6.68 g product (90% yield). After filtration of the mixture, the solvent was evaporated in vacuo to obtain the product as a yellow gum. HPLC retention time was 10.4 minutes (Ultrasphere ODS 5μ, 25 cm×4.6 mm (Beckman); methanol:acetonitrile:water 1559:383:58; 1.5 ml/min; UV 245 nm).

EXAMPLE 4

5,4"-O-Diphenoxyacetyl-doramectin compound of formula (IV) wherein $R^1$ is phenoxyacetyl To a solution of 1 g of the title compound of Example 2 in 20 ml 2-ethoxyethyl ether was added 500 mg calcium carbonate. The mixture was then heated to 185° C. with good agitation while continuously sparging with a nitrogen stream. After 5 hours at 185° C., the mixture was allowed to cool to room temperature and filtered. HPLC analysis of the solution (Ultrasphere ODS 5μ, 25 cm×4.6 mm (Beckman); methanol:acetonitrile:water 559:383:58; 1.5 ml/min; UV 245 nm) showed the presence of 796 mg product (91% yield).

EXAMPLE 5

Doramectin (compound of formula (I))

A solution of 500 mg of the title compound of Example 3 in 1 ml 2-methoxyethyl ether and 3.5 ml methanol was cooled to –35° C. and 2.1 ml 2M methanolic KOH solution was added dropwise over 1 min. The mixture was maintained at –35° C. with good stirring for 1 hour to complete the reaction and then 252 mg glacial acetic acid dissolved in 0.5 ml methanol was added. Cooling was discontinued and 2.2 ml water was added dropwise over 1 hour upon which crystallization commenced. After stirring at ambient temperature for 1 hour, the crystals were collected by filtration, washed with two 0.5 ml portions 7:3 methanol water and dried in a vacuum oven. Recrystallization from methanol/water furnished 272 mg 93.8% pure product (70.6% yield). HPLC retention time was 6.5 minutes (Ultrasphere ODS 5μ, 25 cm×4.6 mm (Beckman); methanol:acetonitrile:water 860:51:89; 1.5 ml/min; UV 245 nm).

EXAMPLE 6

Doramectin (compound of formula (I)

To a solution of 6.6 of the title compound of Example 3 in 75 ml methanol cooled to –15° C. was added 75 ml of saturated solution of ammonia in methanol. The mixture was maintained at –15° C. for 5.5 hours to complete the reaction and then sparged with nitrogen for 30 minutes. The volatiles were removed in vacuo, the resultant light yellow oil was dissolved with 45 ml methanol, and the solution clarified by filtration. To the solution was added, dropwise, 5 ml water upon which crystallization commenced. The mixture was stirred at ambient temperature for 2 hours and then 6.3 ml water was added over 2.5 hours. After further stirring for 1.5 hours the solid was collected by filtration and washed with two 2.5 ml portions of methanol:water (7:3). After drying in a vacuum oven at ambient temperature for 24 hours, 3.75 g of 87.7% pure product (64% yield) was obtained.

EXAMPLE 7

The compound of formula (III) wherein $R^1$ is acetyl and $R^2$ is hydrogen

To a solution of 20 g of the compound of formula (II) in 200 ml methylene chloride under nitrogen was added 28.6 g triethylamine and 1.06 g 4-dimethylaminopyridine. The solution was cooled to –5° to 0° C. and 14.5 g acetic anhydride was added dropwise over 5 minutes. The mixture was maintained at 0° C. for 20 minutes to complete the reaction and then quenched at 0° C. with 200 ml of a saturated solution of sodium bicarbonate. The organic layer was re-extracted twice with saturated sodium bicarbonate, dried ($MgSO_4$), and the solvent removed in vacuo to give 22.2 g of 95% pure product as a white solid (96.7% yield). HPLC retention time was 6.6 minutes (Ultrasphere ODS 5μ, 25 cm×4.6 mm (Beckman); methanol:acetonitrile:water 902:36:62; 1.0 ml/min; UV 245 nm).

EXAMPLE 8

The compound of formula (III) wherein $R^1$ is acetyl and $R^2$ is hydrogen

To a slurry of 5 g of the compound of formula (II) in 100 ml toluene under nitrogen was added 7.24 g triethylamine and 266 mg 4-dimethylaminopyddine. The mixture was cooled to –15° C. and 3.68 g acetic anhydride was added, dropwise, over 5 minutes. The mixture was stirred at –10° C. to –15° C. for 30 minutes to complete the reaction, quenched with 50 ml of saturated aqueous sodium bicarbonate and stirred at ambient temperature for 1 hour. The organic layer was re-extracted twice with 50 ml of saturated aqueous sodium bicarbonate, and dried by partial distillation of the solvent using a Dean-Stark apparatus. The solution was analyzed by HPLC (Ultrasphere ODS 5μ, 25 cm×4.6 mm (Beckman); methanol:acetonitrile:water 902:36:62; 1.0 ml/min; UV 245 nm) and found to contain 5.27g product (96.5% yield).

EXAMPLE 9

The compound of formula (III) wherein $R^1$ is acetyl and $R^2$ is P-tolyloxythiocarbonyl To a solution of 20 g of the title compound of Example 7 in 200 ml ethyl acetate under nitrogen was added 60 ml anhydrous pyridine followed by 22.2 g O-p-tolylchlorothionoformate upon which a yellow precipitate was formed. The mixture was heated to reflux with good agitation for 2 hours to complete the reaction and then cooled to room temperature. The volatiles were removed in vacuo, the residue was partitioned between 150 ml ethyl acetate and 150 ml water, and the organic layer was extracted twice with saturated aqueous sodium bicarbonate and once with water. The ethyl acetate layer was dried (MgSO$_4$) and the solvent removed in vacuo. The residue was dissolved in 25 ml ethyl acetate and 5 ml methylene chloride, the solution was clarified by filtration and chromatographed using a Prep-500 system (Waters Associates) equipped with two silica gel cartridges. The eluting solvent was 70:25:5 hexanes:ethyl acetate:methylene chloride. Fractions containing product were combined and the solvent removed in vacuo to give 19 g (82.6% yield) product as a light yellow solid. HPLC retention time was 17.1 minutes (Ultrasphere ODS 5µ, 25 cm×4.6 mm (Beckman); methanol:acetonitrile:water 902:36:62; 1.0 ml/min; UV 245 nm).

EXAMPLE 10

5,4"-O-Diacetyl-doramectin (compound of formula IV wherein R$^1$ is acetyl)

A suspension of 9.5 g calcium carbonate was heated to 156°–158° C. while continuously sparging with a stream of nitrogen. To this mixture was added 18.7 g of the title compound of Example 9; heating, stirring, and sparging with nitrogen was continued for 25 hours. After cooling to 50° C., the mixture was filtered and the solvent removed in vacuo. The residue was dissolved in 55 ml methylene chloride, 25 ml ethyl acetate and 70 ml hexanes were added, the solution was filtered and chromatographed using a Prep-500 system (Waters Associates) equipped with two silica gel cartridges. The eluting solvent was 70:25:5 hexanes:ethyl acetate:methylene chloride. Fractions containing product were combined and the solvent removed in vacuo to give 13.7 g of 87% pure product as yellow solid (74.8% yield). HPLC retention time was 11.1 minutes (Ultrasphere ODS 5µ, 25 cm×4.6 mm (Beckman); methanol:acetonitrile:water 902:36:62; 1.0 ml/min; UV 245 nm).

EXAMPLE 11

5,4"-O-Diacetyl-doramectin (compound of formula (IV) wherein R$^1$ is acetyl)

To a solution of 504 mg of the title compound of Example 9 in 25 ml 2-ethoxyethyl ether was added 250 mg calcium carbonate. The mixture was then heated to 183°–185° C. with good agitation while continuously sparging with a nitrogen stream. After 1.5 hours at 183°–185° C., analysis of the mixture showed presence of 364.4 mg product (84.7% yield).

EXAMPLE 12

Doramectin (compound of formula (I)

To a solution of 7.3 g of the title compound of Example 10 in 145 ml anhydrous tetrahydrofuran under nitrogen cooled to –72° C., was added 59.5 ml 1.0M lithium triethylborohydride in tetrahydrofuran solution, dropwise, over 45 minutes. The reaction mixture was stirred at –72° to –70° C. for 1 hour and then let slowly warm to room temperature to complete the reaction. The mixture was then quenched with 75 ml water and 75 ml methylene chloride and stirred for 1 hour. The layers were separated, the aqueous layer was extracted with 75 ml methylene chloride, arid the combined organic layers washed twice with 75 ml saturated aqueous sodium bicarbonate. The solvents were evaporated in vacuo, the residue was dissolved in 54 ml methanol, and the solution clarified by filtration. To this solution was added, dropwise over 20 minutes, 6.9 ml water upon which crystallization commenced. The mixture was stirred at ambient temperature for 15 minutes and then 6.2 ml water was added, dropwise over 30 minutes. The mixture was stirred for 18 hours, the solid collected by filtration, washed twice with 2 ml portions of 75:25 methanol:water and dried in a vacuum oven to give 4.27 g of 89.5% pure product (57.3% yield).

EXAMPLE 13

Effect of Nitrogen Sparging on the Thermal Elimination Reaction

To a solution of 5.3 g of the title compound of Example 2 in 55 ml 2-methoxyethyl ether was added 2.5 g calcium carbonate. The mixture was then heated to 157° C. with good agitation while a nitrogen stream was continuously sparged in via a gas dispersion tube. After 30 hours at 154°–157° C., the mixture was allowed to cool to room temperature, filtered and analyzed by HPLC (Ultrasphere ODS 5µ, 25 cm×4.6 mm (Beckman); methanol:acetonitrile:water 559:383:58; 1.5 ml/min; UV 245 nm). The analysis showed the presence of 3.93 g 5,4"-O-diphenoxyacetyl-doramectin (84.8% yield).

This example was repeated under identical conditions, including use of the identical lot of the title compound of Example 2, but with no nitrogen sparging. The yield of product in this case was 47.5%, showing the beneficial effect of nitrogen sparging.

We claim:

1. A compound according to formula (III):

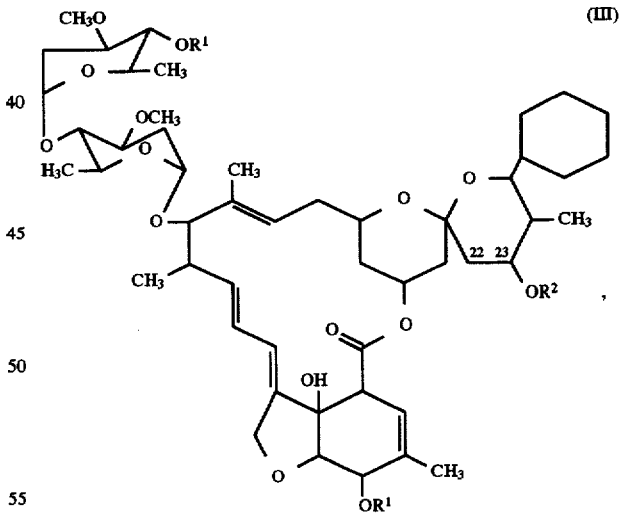

wherein:

R$^1$ is (C$_2$–C$_5$)alkanoyl or aryloxyacetyl; and

R$^2$ is hydrogen or aryloxythiocarbonyl.

2. The compound according to claim 1 wherein R$^1$ is (C$_2$–C$_5$)alkanoyl, phenoxyacetyl or (C$_1$–C$_4$) alkylphenoxyacetyl and R$^2$ is hydrogen or (C$_1$–C$_4$) alkylphenoxythiocarbonyl.

3. The compound according to claim 2 wherein R$^1$ is C$_6$H$_5$OCH$_2$C(=O)—.

4. The compound according to claim 3 wherein R$^2$ is hydrogen.

5. The compound according to claim 3 wherein $R^2$ is p-$CH_3$—$C_6H_5OC(=S)$—.

6. The compound according to claim 2 wherein $R^1$ is $CH_3C(=O)$—.

7. The compound according to claim 6 wherein $R^2$ is hydrogen.

8. The compound according to claim 6 wherein $R^2$ is p-$CH_3$—$C_6H_5OC(=S)$—.

9. A compound according to formula (IV):

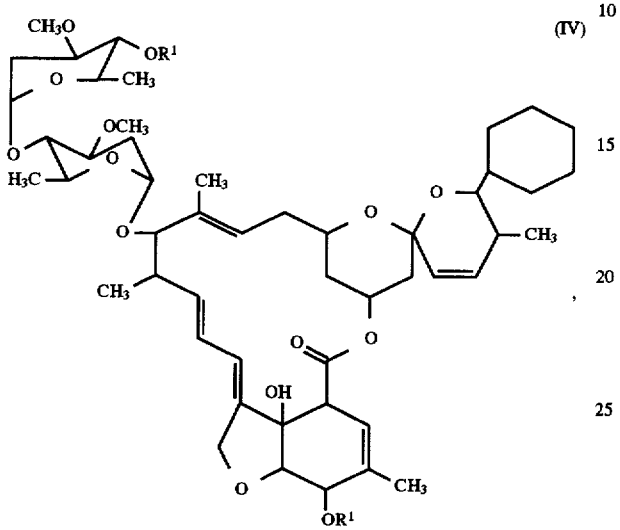

(IV)

wherein $R^1$ is ($C_2$-$C_5$)alkanoyl or aryloxyacetyl.

10. The compound according to claim 9 wherein $R^1$ is ($C_2$-$C_5$)alkanoyl, phenyoxyacetyl or ($C_1$-$C_4$) alkylphenoxyacetyl.

11. The compound according to claim 10 wherein $R^1$ is $CH_3C(=O)$—.

12. The compound according to claim 10 wherein $R^1$ is $C_6H_5OCH_2C(=O)$—.

13. A process for preparing a compound of the formula (I)

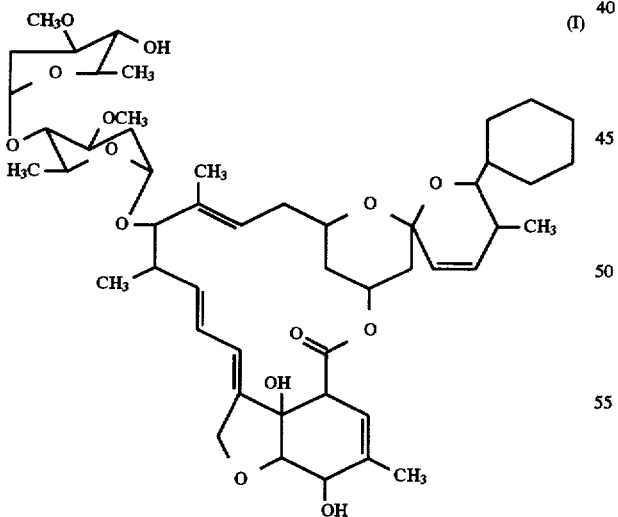

(I)

comprising the consecutive steps of (a) reacting a compound of the formula (II)

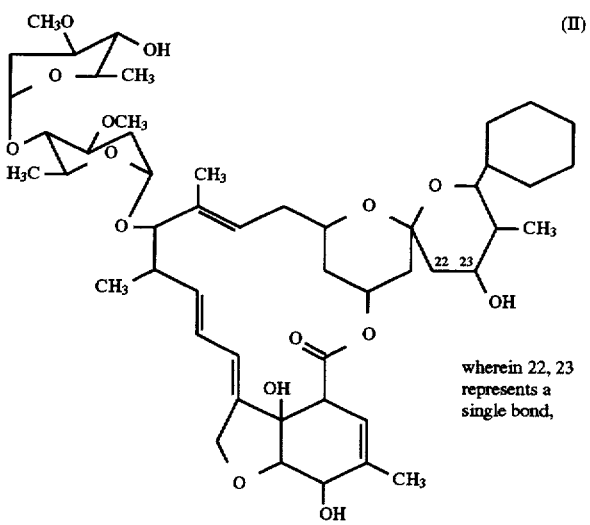

(II)

wherein 22, 23 represents a single bond, with an acylating agent of the formula ($R^4CO$)$_2O$ or $R^4COX$ wherein $R^4$ is aryloxymethyl and X is Cl or Br to form a compound according to formula (III)

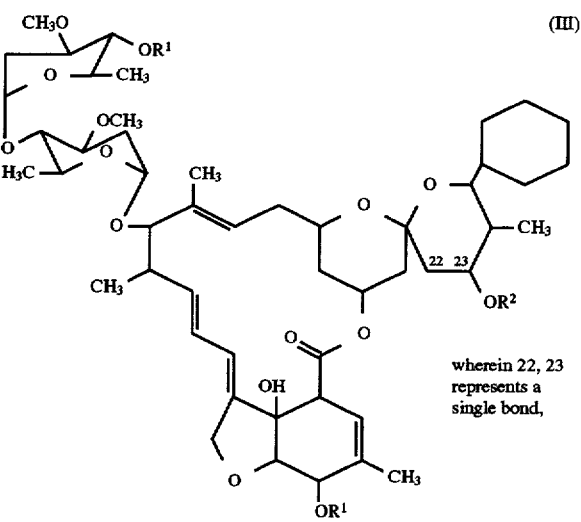

(III)

wherein 22, 23 represents a single bond, wherein $R^1$ is aryloxyacetyl and $R^2$ is hydrogen;

(b) reacting said compound of formula (III) wherein $R^1$ is aryloxyacetyl and $R^2$ is hydrogen with a compound of the formula $R^3OC(=S)X$ wherein $R^3$ is aryl and X is Cl or Br to form a compound according to formula (III) wherein $R^1$ is aryloxyacetyl and $R^2$ is aryloxythiocarbonyl;

(c) reacting said compound of formula (III) wherein $R^1$ is aryloxyacetyl and $R^2$ is aryloxythiocarbonyl in a reaction inert solvent at from about 150° C. to about 200° C. for about 2 hours to about 48 hours in the presence of calcium carbonate under continuous reaction inert gas sparging to form a compound according to formula (IV)

(a) reacting a compound of the formula (II)

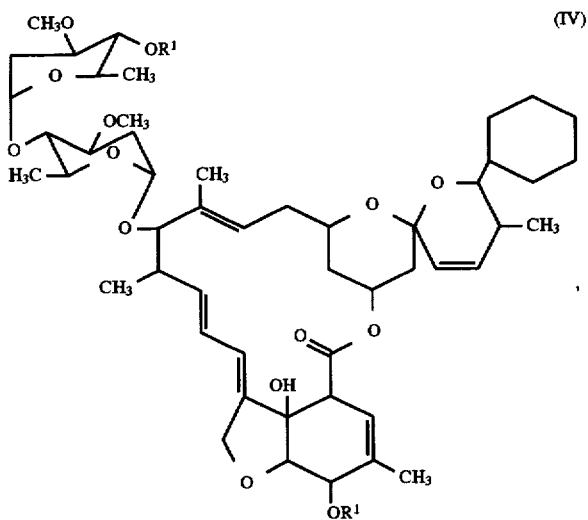

(IV)

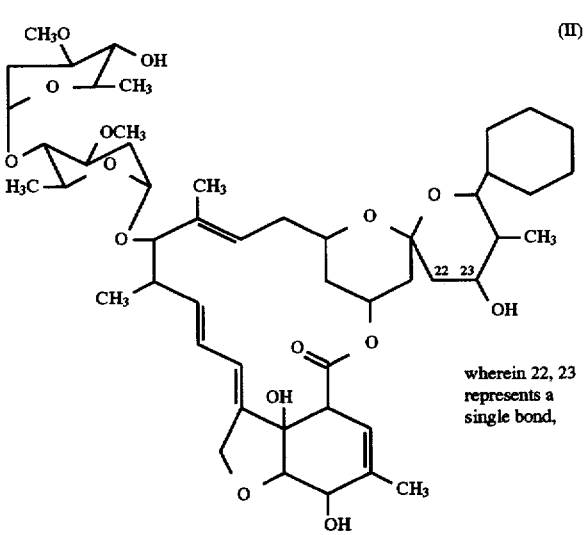

(II)

wherein 22, 23 represents a single bond, wherein $R^1$ is aryloxyacetyl; and with an acylating agent of the formula $(R^4CO)_2O$ or $R^4COX$ wherein $R^4$ is $(C_1-C_4)$alkyl and X is Cl or Br to form a compound according to formula (III)

(d) reacting said compound of formula (IV) wherein $R^1$ is aryloxyacetyl with a base in an alcohol solvent to form the compound according to formula (I).

14. The process according to claim 13 wherein the reaction inert gas is nitrogen.

15. The process according to claim 14 wherein the base is $NH_3$, KOH, KCN, $Na_2CO_3$, $NaHCO_3$ or NaOAc.

16. A process for preparing a compound of formula (I)

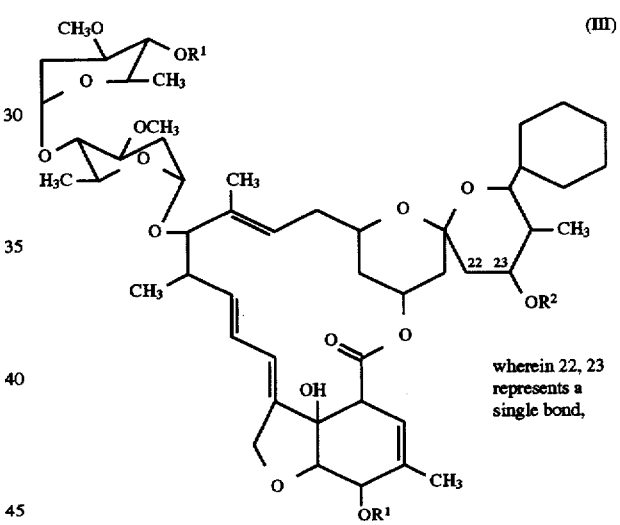

(III)

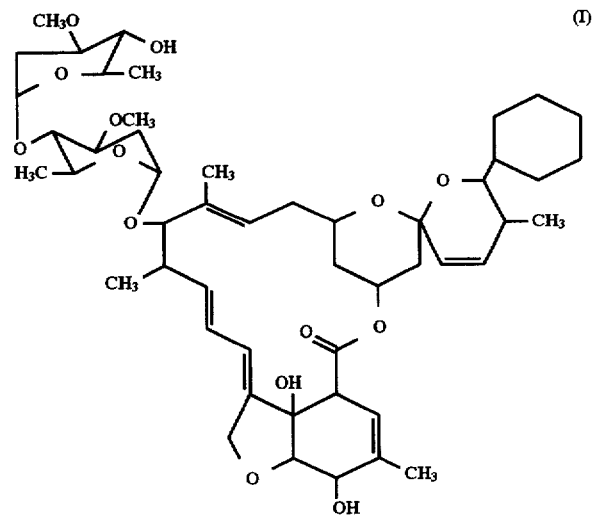

(I)

wherein $R^1$ is $(C_1-C_4)$alkanoyl and $R^2$ is hydrogen;

wherein 22, 23 represents a single bond, (b) reacting said compound of formula (III) wherein $R^1$ is $(C_1-C_4)$alkanoyl and $R^2$ is hydrogen with a compound of the formula $R^3OC(=S)X$ wherein $R^3$ is aryl and X is Cl or Br to form a compound according to formula (III) wherein $R^1$ is $(C_1-C_4)$alkanoyl and $R^2$ is aryloxythiocarbonyl;

(c) reacting said compound of formula (III) wherein $R^1$ is $(C_1-C_4)$alkanoyl and $R^2$ is aryloxythiocarbonyl in a reaction inert solvent at from about 150° C. to about 200° C. for about 2 hours to about 48 hours in the presence of calcium carbonate under continuous reaction inert gas sparging to form a compound according to formula (IV)

comprising the consecutive steps of

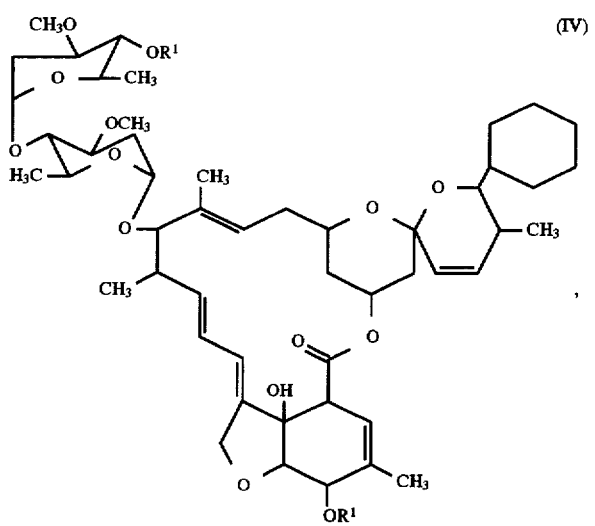

(IV)

wherein $R^1$ is $(C_1$-$C_4)$alkanoyl; and (d) reacting said compound of formula (IV) wherein $R^1$ is $(C_1$-$C_4)$alkanoyl with a lithium aluminum hydride, sodium cyanoborohydride or lithium triethylborohydride in a reaction inert solvent to form the compound according to formula (I).

17. The process according to claim 16 wherein the inert gas is nitrogen.

18. The process according to claim 17 comprising reacting said compound of formula (IV) wherein $R^1$ is $(C_1$-$C_4)$ alkanoyl with lithium triethylborohydride.

19. The process according to claim 18 comprising mixing said compound of formula (IV) wherein $R^1$ is $(C_1$-$C_4)$ alkanoyl with said lithium triethylborohydride at a temperature of −78° C. to −70° C., maintaining said temperature at −78° C. to −70° C. for 15 minutes to one hour and then adjusting said temperature to ambient temperature.

20. A process for preparing a compound of formula (IV)

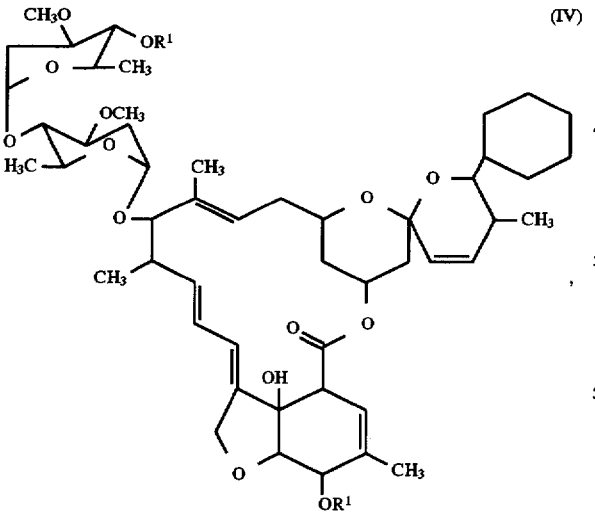

(IV)

wherein $R^1$ is $(C_2$-$C_5)$alkanoyl or aryloxyacetyl comprising reacting a compound of formula (III)

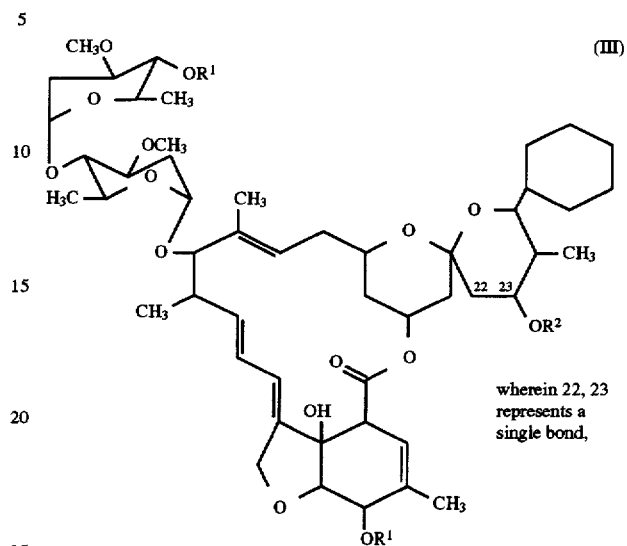

(III)

wherein 22, 23 represents a single bond, wherein $R^1$ is $(C_2$-$C_5)$alkanoyl or aryloxyacetyl and $R^2$ is aryloxythiocarbonyl in a reaction inert solvent at from about 150° C. to about 200° C. for about 2 hours to about 48 hours in the presence of calcium carbonate under continuous reaction inert gas sparging.

21. The process according to claim 20 wherein the reaction inert gas is nitrogen.

22. A method of treating a mammal suffering from a parasitic disease or diseases comprising administering to said mammal an antiparasitic effective amount of a compound according to claim 1.

23. A method of treating a mammal suffering from a parasitic disease or diseases comprising administering to said mammal an antiparasitic effective amount of a compound according to claim 9.

* * * * *